United States Patent [19]
Reneau

[11] Patent Number: 4,633,859
[45] Date of Patent: Jan. 6, 1987

[54] INERT GAS ENVIRONMENTAL CONTROL SYSTEM FOR A HYPERBARIC CHAMBER AND A METHOD FOR DOING SAME

[75] Inventor: Raymond P. Reneau, Houston, Tex.

[73] Assignee: Keyes Offshore, Inc., Sugar Land, Tex.

[21] Appl. No.: 549,482

[22] Filed: Nov. 4, 1983

[51] Int. Cl.[4] .............................................. A61M 16/02
[52] U.S. Cl. .................................................. 128/205.26
[58] Field of Search ....................... 128/204.29, 205.11, 128/206.26, 205.22

[56] References Cited

U.S. PATENT DOCUMENTS 3,547,118 12/1970 Kolman et al. ................ 128/205.26
3,587,438 6/1971 Foster et al. .................. 128/204.22
3,680,557 8/1972 Donigvian ...................... 128/205.26
3,754,551 8/1973 Nielsen ........................... 128/205.26
4,274,405 6/1981 Schmidt et al. ................ 128/205.26
4,452,242 6/1984 Bänziger .......................... 128/205.26

*Primary Examiner*—Andrew H. Metz
*Assistant Examiner*—Glenn A. Caldarola
*Attorney, Agent, or Firm*—Glaser, Griggs & Schwartz

[57] ABSTRACT

A control system for a hyperbaric chamber and method for doing same which provides for an initial purging of a portion of the oxygen contained in the air within the chamber until an analyzer detects that the oxygen concentration has been reduced below the oxygen concentration of air at one atmosphere absolute pressure. Having reduced the oxygen concentration within the chamber using a pressurized inert gas, valves are operated to pressurize the chamber at a desired rate to a desired value. The patient within the chamber is connected to an independent breathing system where breathing gas is delivered to the patient at substantially the same pressure as the pressure in the hyperbaric chamber.

4 Claims, 1 Drawing Figure

INERT GAS ENVIRONMENTAL CONTROL SYSTEM FOR A HYPERBARIC CHAMBER AND A METHOD FOR DOING SAME

FIELD OF THE INVENTION

The field of this invention relate to hyperbaric chambers used for medical applications, and in particular, relates to environmental control systems therefor.

DESCRIPTION OF THE PRIOR ART

In the past, hyperbaric chambers were pressurized with oxygen, air or other gases so that at all times the environment within the hyperbaric chamber was an oxygen-enriched atmosphere at increased pressure levels. In an oxygen-enriched atmosphere the percentage of oxygen or oxygen and nitrous oxide is greater than the quotient of 23.45 divided by the square root of the total pressure in atmospheres. Having an oxygen-enriched atmosphere under pressure within a hyperbaric chamber presented enhanced risks of fire. Any spark source such as static electricity or arcing within monitoring devices found within such hyperbaric chambers could ignite the pressurized oxygen within the chamber and cause a catastrophic fire. To avoid the potential of combustion within a hyperbaric chamber, prior art devices had to eliminate all spark producing devices or instruments from the chamber interior or in the alternative purge all the instrument enclosures with an inert gas to prevent ignition. These additional precautions greatly increased the cost of such devices and were not in all cases fail-safe in design.

SUMMARY OF THE INVENTION

A control system for a hyperbaric chamber and method of doing same which provides for an initial purging of a portion of the oxygen contained in the air within the chamber until an analyzer detects that the oxygen concentration has been reduced below the oxygen concentration of air at one atmosphere absolute pressure. Having reduced the oxygen concentration within the chamber using a pressurized inert gas, valves are operated to pressurize the chamber at a desired rate to a desired value. The patient within the chamber is connected to an independent breathing system where breathing gases are delivered to the patient at substantially the same pressure as the pressure in the hyperbaric chamber.

DESCRIPTION OF THE PREFERRED EMBODIMENT

Figure 1:
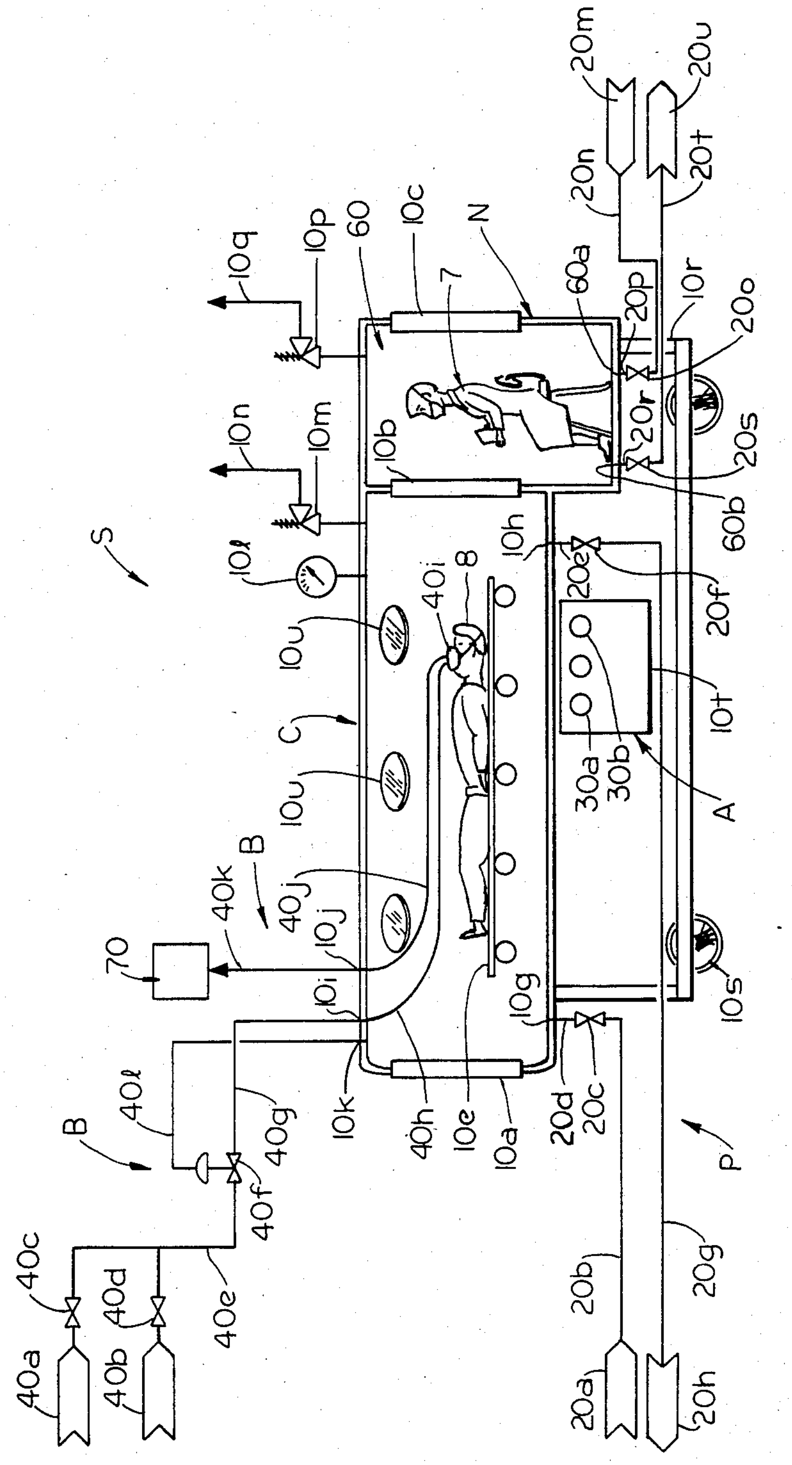
FIG. 1 is a sectional, elevational, schematic view, of a typical hyperbaric chamber and attached attendant chamber, utilizing the inert gas environmental control system of the present invention.

The environmental control system of the present invention is designated generally by the letter S. The control system S is used generally with a hyperbaric chamber C, and includes generally purge means P, analyzer means A, and patient breathing means B.

As schematically shown, the hyperbaric chamber C has an end closure 10*a* which may be of any suitable type. An attendant compartment N is connected at one end of hyperbaric chamber C via interconnecting door 10*b*. Attendant compartment N has an exterior door 10*c* to permit an attendant 7 rapid entry into attendant compartment N as will be more fully described hereinbelow. The gourney 10*e* supports the patient 8 within hyperbaric chamber C and facilitates insertion or removal of the patient 8 through end door 10*a*.

Hyperbaric chamber C further contains a pressurizing inlet 10*g* located adjacent end closure 10*a* and mounted to the bottom of hyperbaric chamber C which may include an orientation perpendicular to the longitudinal axis of the hyperbaric chamber C. An outlet 10*h* may be located at the bottom of hyperbaric chamber C at the opposite end from pressurizing inlet 10*g* and adjacent attendant compartment N or at any other suitable location. The outlet 10*h* may be oriented in a plane perpendicular to the longitudinal axis of the hyperbaric chamber C. As such, both the pressurizing inlet 10*g* and outlet 10*h* may be mounted on the hyperbaric chamber C at an elevation below the patient 8, as will be more fully discussed hereinbelow. The attendant compartment N includes compartment 60, which in similar fashion to the hyperbaric chamber C, includes a pressurizing inlet 60*a* and outlet 60*b*.

Hyperbaric chamber C contains patient breathing inlet 10*i* and patient breathing outlet 10*j* shown in FIG. 1 to be preferably mounted in the top of hyperbaric chamber C. It is understood that the mounting location for patient breathing inlet 10*i* and patient breathing outlet 10*j* may be placed elsewhere along hyperbaric chamber C without departing from the spirit of the invention. A sensing connection 10*k* is located in hyperbaric chamber C and is used with patient breathing means B as will be more fully described hereinbelow. It is understood that analyzer means A is in fluid communication with hyperbaric chamber C in order to enable analyzer means A to sample and analyze the gases in hyperbaric chamber C.

A pressure gauge 10*l* is mounted with the hyperbaric chamber C to indicate the operating pressure therewithin. A safety relief valve 10*m* is connected to hyperbaric chamber C in order to prevent overpressurization. The outlet line 10*n* is piped to a suitable location where it will not present a danger to personnel or equipment. A safety relief valve 10*p* is in fluid communication with attendant compartment N and has an outlet line 10*q* piped to a location away from personnel or equipment.

The hyperbaric chamber C and the connected attendant compartment N are supported by a frame 10*r* which may be mounted on casters 10*s* or alternatively fixed in position. Therefore, using frame 10*r* and casters 10*s*, hyperbaric chamber C and the attached attendant chamber N can be manually moved about as necessary or, in the alternative, be self-propelled using an electric motor (not shown) mounted to frame 10*r*, to drive casters 10*s*.

A control panel 10*t* is shown schematically as mounted adjacent hyperbaric chamber C and provides a convenient place for mounting all the necessary monitoring equipment as well as analyzer means A. Alternatively, such equipment may be mounted on the frame 10*r*, atop the chamber C or removably mounted, as desired.

Hyperbaric chamber C and attendant compartment N are constructed of a materials suitable to withstand the design pressures of five to six atmospheres absolute. A stainless steel material is best suited for this application as it provides excellent impact, heat, and corrosion resistance. Windows 10*u* are disposed along hyperbaric chamber 10*c* to allow viewing of the patient 8.

In case of emergencies while hyperbaric chamber C is under pressure, an attendant 7 may quickly open exterior door 10*c* and enter attendant compartment N. Having entered attendant compartment N, the attendant 7 would close exterior door 10*c* and equalize the pressure between hyperbaric chamber C and attendant compartment N as discussed below. The air initially present in attendant compartment N is sufficient for the attendant 7 to breathe without using a separate breathing system. Preferably the pressure between attendant compartment N and hyperbaric chamber C is equalized with inert gases and thereafter, the attendant 7 can open interconnecting door 10*b* for access to the patient 8 within hyperbaric chamber C, with the hyperbaric chamber C remaining in a pressurized state.

The control system S of the present invention includes purge means P which further includes an inert pressurized gas source 20*a* which is in fluid communication with pressurizing inlet 10*g*. Conduit 20*b* connects inert pressurized gas source 20*a* to throttling valve 20*c*. Conduit 20*d* connects throttling valve 20*c* to pressurizing inlet 10*g*. It is understood that any inert gas may be used as the inert pressurized gas source 20*a*, although the preferred gases are nitrogen or helium. It is further understood that inert pressurized gas source 20*a* has been regulated to a pressure below the maximum design pressure of hyperbaric chamber 10*c* or attendant compartment N. Typically, for the range of pressures encountered in hyperbaric therapy, the hyperbaric chamber C and the attendant chamber N are designed to withstand five to six atmospheres absolute pressure.

Conduit 20*e* connects outlet 10*h* to valve 20*f*. Conduit 20*g* is connected to valve 20*f* and has a terminus 20*h* at a point away from personnel or equipment. Valve 10*f* is operated either in the closed or open position. In the open position it permits purging of hyperbaric chamber C when throttling valve 20*c* is opened thereby permitting inert pressurized gas to enter hyperbaric chamber C from source 20*a*. When valve 20*f* is in the closed position, throttling valve 20*c* may be used to regulate the rate of buildup of pressure within hyperbaric chamber C and ultimately control the pressure in hyperbaric chamber C at a desired value.

In similar fashion, the attendant compartment N may be pressurized by connecting a pressurized gas source 20*m* through conduit 20*n*, throttling valve 20*o*, and conduit 20*p* to the pressurizing inlet 60*a*. The outlet 60*b* is in flow communication with conduit 20*r*, valve 20*s*, and conduit 20*t*, whereafter such is connected to terminus 20*u* located at a point away from personnel and equipment. The pressurization of the attendant compartment N may be accomplished independent of pressurization of the hyperbaric chamber C, by proper operation of valves 20*o*, 20*s* in a fashion similar to the operation of valves 20*c*, 20*f*.

The control system S of the present invention further includes analyzer means A. Preferably, the analyzer means A includes an oxygen analyzer 30*a* which may be mounted with control panel 10*t* and is in fluid communication with hyperbaric chamber C. The oxygen analyzer 30*a* is one of many types well known in the art. Throttling valve 20*c* and valve 20*f* may be manually manipulated based on the readings obtained on the oxygen analyzer 30*a*, or in the alternative, the purging and pressurization of hyperbaric chamber C may be automatically controlled by oxygen analyzer 30*a* by incorporating control circuitry of a type well known in the art. In automatic operation, throttling valve 20*c* and valve 20*f* would have external operators which would be actuated based on the readings obtained by the oxygen analyzer 30*a* as well as a pressure controller (not shown). The pressure controller monitors the rate of pressure buildup after valve 20*f* has been closed and regulates valve 20*c* to hold the pressure at the preset value. Additionally, an oxygen analyzer 30*b* may similarly be in fluid communication with the attendant compartment N for like manual or automatic operation, as desired.

In order to reduce fire hazards in hyperbaric chamber C, the control system S of the present invention provides the major advantage of reducing the oxygen concentration within hyperbaric chamber C before pressurization. Accordingly, the patient 8 is inserted into hyperbaric chamber C via gourney 10*e* through the open end closure 10*a*. Having inserted the patient 8 into hyperbaric chamber C, the closure 10*a* is closed. At that time hyperbaric chamber C is full of air. If the air present in the hyperbaric chamber C is compressed to above several atmospheres, it presents an atmosphere within hyperbaric chamber C that will promote rapid combustion in the presence of a spark. Such a spark may come from static electricity or arcing within electrical devices mounted within hyperbaric chamber C.

In order to minimize the fire hazard within hyperbaric chamber C, it is advantageous to reduce the oxygen concentration to less than the concentration of oxygen present in air at one atmosphere absolute pressure. By way of example, one-half to three-fourths of the oxygen concentration of air at one atmosphere absolute pressure is preferred. Since the flammability of the gaseous mixture within hyperbaric chamber C is directly proportional to the percentage of oxygen found therein, an initial purging step which displaces the air initially found in hyperbaric chamber C with an inert gas greatly reduces the possibility of ignition from a spark.

In purging hyperbaric chamber C, throttling valve 20*c* is slowly opened while valve 20*f* is fully open. Inert gas flows from inert pressurized gas source 20*a* through conduit 20*b*, throttling valve 20*c*, conduit 20*d*, and into hyperbaric chamber C via pressurizing inlet 10*g*. The air in hyperbaric chamber C may be displaced in a direction along the longitudinal axis of hyperbaric chamber C by the flow of inert gas from pressurizing inlet 10*g* to outlet 10*h*. It is desired that the flow of inert gas from pressurizing inlet 10*g* to outlet 10*h* be in a flow regime capable of effectively displacing the air initially within hyperbaric chamber C and capable of preventing separation of air within the hyperbaric chamber C. It is desired that the pressurized inert gas from the pressurizing inlet 10*g* insure proper purging of air from within the hyperbaric chamber C without stratification of air-/inert gases within the chamber. Proper mixing of the incoming pressurized inert gases with the air within the hyperbaric chamber C is important for proper purging of the air from the hyperbaric chamber C. A similar result is also desired in pressurizing and purging the attendant compartment N, when necessary.

The displacement process is continued until oxygen analyzer 30*a* indicates the oxygen concentration within hyperbaric chamber C has been reduced below the oxygen concentration found in air at one atmosphere absolute pressure. Having attained the appropriate reading on oxygen analyzer 30*a*, valve 20*f* is closed thereby initiating pressurization within hyperbaric chamber C as additional inert gas enters hyperbaric chamber C from inert pressurized gas source 20a.

As shown in FIG. 1, the position of throttling valve 20c can be adjusted while observing the reading on pressure gauge 101. By manipulation of throttling valve 20c with valve 20f in the closed position, the rate of pressurization of hyperbaric chamber 10c can be controlled using pressure gauge 10l as feedback. Having attained the desired pressurization for the treatment of the patient 8, throttling valve 20c is closed thereby preventing further pressure buildup within hyperbaric chamber C. It is to be understood that a pressure controller may be employed to sense the pressure in hyperbaric chamber C and regulate the position of throttling valve 20c thereby controlling the rate of pressure buildup as well as the final set pressure within hyperbaric chamber C, without departing from the spirit of the invention.

The control system S of the present invention further includes patient breathing means B which is connected to the patient 8 within hyperbaric chamber C. Patient breathing means B effectively isolates the gases breathed by patient 8 from the pressurized gases within hyperbaric chamber C. Patient breathing means B comprises of a pressurized oxygen source 40a and a pressurized air source 40b. Both pressurized oxygen source 40a and pressurized air source 40b are regulated to deliver gas at pressures below the maximum operating pressure of hyperbaric chamber C. Both pressurized oxygen source 40a and pressurized air source 40b are in fluid communication with patient breathing inlet 10i on hyperbaric chamber C. Valve assemblies 40c and 40d are used to selectively connect pressurized oxygen source 40a or pressurized air source 40b to patient breathing inlet 10i. Valve assemblies 40c and 40d serve the additional function of preventing backflow of pressurized air toward pressurized oxygen source 40a as well as preventing oxygen flow toward pressurized air source 40b. In normal operation, valve assembly 40c is in the open position and valve assembly 40d is in the closed position thereby allowing oxygen to flow from pressurized oxygen source 40a to patient breathing inlet 10i.

Two types of breathing systems may be employed in furnishing oxygen to the patient 8. The two types of supply systems are known in the art as demand and positive free flow. FIG. 1 illustrates a demand system although it is understood that a positive free flow system can be used without departing from the spirit of the invention. Conduit 40e connects valve assemblies 40c and 40d to regulator valve 40f. Regulator valve 40f is connected to hyperbaric chamber C by conduit 40g. Flexible extension conduit 40h extends from patient breathing inlet 10i to mask 40i which covers the mouth and nose of patient 8. Flexible extension conduit 40h is in fluid communication with conduit 40g thereby allowing compressed oxygen or air to enter mask 40i. Flexible extension conduit 40j connects mask 40i with patient breathing outlet 10j. Located within mask 40i is a diaphragm (not shown) of a type well known in the art, which is in fluid communication with flexible extension conduit 40j. Vent line 40k directs gases exhaled from mask 40i via flexible extension conduit 40j to a safe point away from personnel or equipment. A gas concentration analyzer of a type well known in the art, shown schematically as analyzer 70, may be connected to vent line 40k to aid in monitoring the condition of patient 8. The readings from the analyzer 70 sampling the gases exhaled from patient 8 can be indicated and recorded on control panel 10t or elsewhere as desired.

In order to permit patient 8 to breathe normally and further in order to prevent collapsing, flexible extension conduits 40h and 40j, it is advantageous to have the pressure within flexible extension conduits 40h and 40j at approximately the same pressure as the pressure within hyperbaric chamber C which acts on the outer walls of flexible extension conduits 40h and 40j. In order to establish a pressure equalization, a sensing line 401 connects sensing connection 10k to regulator valve 40f. Regulator valve 40f, being exposed to the pressure in hyperbaric chamber C adjusts itself to regulate the pressure in conduit 40g below the pressure within hyperbaric chamber 10c. If the patient neither inhales nor exhales, the diaphragm (not shown) retains a pressure within mask 40i below the pressure in hyperbaric chamber C. This type of breathing system is called a demand system because only when patient 8 inhales thereby reducing the pressure in mask 40i, will regulator valve 40f admit additional oxygen or air (depending on the position of valve assemblies 40c and 40d) to flow toward mask 40i. The patient 8 may then exhale by forcing gas through the diaphragm (not shown) through flexible extension conduit 40j and out of hyperbaric chamber C through vent line 40k.

In a positive free flow breathing system regulator valve 40f would be positioned on vent line 40k and be adapted to sense the pressure within hyperbaric chamber C via sensing line 40l. Therefore, the pressurized oxygen source 40a or the pressurized air source 40b would be directly connected to mask 40i via conduit 40e, conduit 40g, patient breathing inlet 10i, and flexible extension conduit 40h. A diaphragm in mask 40i would not be required. Regulator 40f, now mounted in vent line 40k senses the pressure in hyperbaric chamber C and regulates the pressure in mask 40i above the pressure within hyperbaric chamber C acting on the outside of mask 40i. Accordingly, there is a positive free flow of oxygen or air from either the pressurized oxygen source 40a or the pressurized air source 40b to the mask 40i mounted to patient 8 within hyperbaric chamber C. By exhaling, the patient 8 builds up the pressure in mask 40i which in turn causes fluid flow from mask 40i through flexible extension conduit 40j, through patient breathing outlet 10j, to vent line 40k and past regulator valve 40f.

Further, by use of the control system S of the present invention, should the patient 8 experience oxygen toxicity while under pressure within the hyperbaric chamber C, the patient's mask 40i need only be removed. As such, the inert gas-rich atmosphere within the hyperbaric chamber C will tend to draw the excess oxygen from the oxygen-toxic patient 8, to enhance recovery therefrom.

Thus by utilizing the environmental control system S of the present invention, the concentration of oxygen within the air in the hyperbaric chamber C is initially reduced and thereafter the hyperbaric chamber C is pressurized with an inert gas other than oxygen. This reduces dramatically the potential fire hazards due to the presence of oxygen under pressure. The consumption of oxygen is also greatly reduced due to the use of inert gas such as nitrogen, helium or other inert gases as may be medically appropriate in the pressurization process. Furthermore, the risk of fire from a spark within the hyperbaric chamber C is reduced use of the environmental control system S due to the lower combustibility of the gas mixture within the hyperbaric chamber C.

The foregoing disclosure and description of the invention are illustrative and explanatory thereof, and various changes in the size, shape and materials, as well as in the details of the illustrated construction may be made without departing from the spirit of the invention.

I claim:

1. A method for controlling the environment inside a hyperbaric chamber to reduce combustibility therein, the chamber having a patient therein, the method comprising the steps of:

connecting the patient to a breathing system which delivers breathing gases to the patient at pressures substantially equal to the pressure in the chamber;

displacing a portion of the oxygen in the air initially in the chamber using a pressurized inert gas by initially opening a first valve at an outlet connection to the chamber and thereafter opening a second valve at the pressurizing inlet to the chamber;

controlling the movement of the first and second valves for sequentially opening the first valve, and then opening the second valve;

analyzing the oxygen concentration in the chamber to detect a drop in oxygen concentration;

pressurizing the chamber with pressurized inert gas; and, closing the first valve when the oxygen concentration has been reduced below the oxygen concentration in air at one atmosphere absolute.

2. The method of claim 1 further including the step of:

regulating the second valve after closing the first valve to control the rate of pressure buildup in the hyperbaric chamber.

3. The method of claim 2, further including the step of:

selecting between pressurized oxygen and other pressurized gases as the breathing gas source to be connected to the patient.

4. A method for controlling the environment inside a hyperbaric chamber to reduce combustibility therein, the chamber having a patient therein, comprising the steps of:

displacing a portion of the oxygen in the air initially in the chamber using a pressurized inert gas by initially opening a first valve at an outlet connection to the chamber and thereafter opening a second valve at the pressurizing inlet to the chamber;

connecting the patient to a breathing system which delivers breathing gases to the patient at pressures substantially equal to the pressure in the chamber;

controlling the movement of the first and second valves for sequentially opening the first valve, and then opening the second valve;

analyzing the oxygen concentration in the chamber to detect a drop in oxygen concentration;

pressurizing the chamber with pressurized inert gas; and, closing the first valve when the oxygen concentration has been reduced below the oxygen concentration in air at one atmosphere absolute.

* * * * *